(12) United States Patent
Salinas et al.

(10) Patent No.: US 11,992,631 B2
(45) Date of Patent: May 28, 2024

(54) SERVICE LOOP RING

(71) Applicant: Boston Scientific Scimed Inc., Maple Grove, MN (US)

(72) Inventors: Alvin Salinas, San Marcos, CA (US); Eric A. Schultheis, San Clemente, CA (US); Nelson Lim, San Diego, CA (US); Thanh Tran, Chula Vista, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 17/032,903

(22) Filed: Sep. 25, 2020

(65) Prior Publication Data
US 2021/0093833 A1 Apr. 1, 2021

Related U.S. Application Data

(60) Provisional application No. 62/907,204, filed on Sep. 27, 2019.

(51) Int. Cl.
| | | |
|---|---|---|
| *A61B 18/02* | (2006.01) | |
| *A61M 25/01* | (2006.01) | |
| *A61M 25/09* | (2006.01) | |
| *A61M 25/10* | (2013.01) | |
| *A61B 18/00* | (2006.01) | |

(52) U.S. Cl.
CPC .... *A61M 25/0147* (2013.01); *A61M 25/0122* (2013.01); *A61M 25/0136* (2013.01); *A61M 25/0138* (2013.01); *A61M 25/0155* (2013.01); *A61M 25/09* (2013.01); *A61M 25/10* (2013.01); *A61M 25/1018* (2013.01); *A61M 25/1025* (2013.01); *A61B 2018/0091* (2013.01); *A61B 18/02* (2013.01); *A61M 2025/0163* (2013.01); *A61M 2025/09133* (2013.01); *A61M 2025/1043* (2013.01)

(58) Field of Classification Search
CPC .. A61M 2025/1043; A61M 2025/1061; A61M 25/1025; A61M 25/1018; A61M 25/0147; A61M 25/0136; A61B 2018/0212
See application file for complete search history.

(56) References Cited

U.S. PATENT DOCUMENTS

| | | | | |
|---|---|---|---|---|
| 5,439,006 A | * | 8/1995 | Brennen | A61M 25/0136 |
| | | | | 604/95.04 |
| 7,871,395 B2 | | 1/2011 | Hu et al. | |
| 2007/0010801 A1 | * | 1/2007 | Chen | A61M 25/0147 |
| | | | | 606/1 |

(Continued)

FOREIGN PATENT DOCUMENTS

WO  WO-2012084264 A1 * 6/2012 ......... A61B 1/00131

*Primary Examiner* — Ariana Zimbouski
*Assistant Examiner* — Anna E Goldberg-Richmeier
(74) *Attorney, Agent, or Firm* — Nelson Mullins Riley & Scarborough LLP

(57) ABSTRACT

A medical device including a catheter body, a first elongate body, and a service loop ring. The catheter body has a catheter shaft. The first elongate body extends through at least part of the catheter shaft and is configured to move longitudinally in the catheter shaft. The first elongate body is looped through the service loop ring to form a service loop configured to expand and contract as the first elongate body moves longitudinally in the catheter shaft.

13 Claims, 8 Drawing Sheets

(56) References Cited

U.S. PATENT DOCUMENTS

| | | | |
|---|---|---|---|
| 2008/0097373 A1* | 4/2008 | Hu | A61M 25/1025 604/500 |
| 2010/0121147 A1* | 5/2010 | Oskin | A61B 1/0051 604/528 |
| 2019/0167331 A1* | 6/2019 | Schultheis | A61B 18/02 |

* cited by examiner

# SERVICE LOOP RING

CROSS REFERENCE TO RELATED APPLICATION

This application claims priority to Provisional Application No. 62/907,204, filed Sep. 27, 2019, which is herein incorporated by reference in its entirety.

TECHNICAL FIELD

The present disclosure relates to medical devices. More specifically, the present disclosure relates to providing extension and retraction of one or more wires and/or conduits in a medical device.

BACKGROUND

Medical devices for minimally invasive surgery are the tools of choice for some surgical procedures, such as at least some ablation and dilation procedures. Often, these medical devices include catheters or similar devices that are introduced into the patient's body through blood vessels or other parts of the patient's body and steered to a site of interest. Each medical device may include one or more guide wires, fluid conduits, steering wires, and other wires and conduits. During surgery, these wires and conduits may experience periods of being slack or under tension, such that some medical devices are configured to take up the slack and relieve the tension by retracting or extending the wire or conduit.

In some medical devices, the wire or conduit is formed into a loop, referred to as a service loop, for accommodating the extension and retraction of the wire or conduit. In some devices, the service loop is wound around a support post or confined in a small section in the medical device. However, this support post/confinement section may limit the ability of the service loop to close as small as possible for extending the wire or conduit, and the support post/confinement section may limit the ability of the service loop to expand as large as possible to accommodate retracting the wire or conduit into the medical device. In addition, a support post for the service loop can be very costly to make due to manufacturing and assembling of complicated injection molded parts.

SUMMARY

In an Example 1, a medical device including a catheter body having a catheter shaft, a first elongate body that extends through at least part of the catheter shaft and is configured to move longitudinally in the catheter shaft, and a service loop ring. Wherein the first elongate body is looped through the service loop ring to form a service loop configured to expand and contract as the first elongate body moves longitudinally in the catheter shaft.

Example 2 is the medical device of Example 1, wherein the service loop ring is a tubular piece of material.

Example 3 is the medical device of any of Examples 1 and 2, including a housing coupled to the catheter shaft and wherein the service loop ring and the service loop are disposed in the housing.

Example 4 is the medical device of any of Examples 1-3, wherein the first elongate body is a fluid injection coil.

Example 5 is the medical device of any of Examples 1-4, including a second elongate body that extends through at least part of the catheter shaft and has a distal end that protrudes from the catheter shaft, wherein the second elongate body is configured to move longitudinally in the catheter shaft and a distal end of the first elongate body is engaged adjacent the distal end of the second elongate body.

Example 6 is the medical device of Example 5, including a handle and an element movably coupled to the handle, wherein the element is coupled to the second elongate body to move the second elongate body longitudinally in the catheter shaft.

Example 7 is the medical device of any of Examples 5 and 6, including an expandable member having a proximal end attached to a distal end of the catheter shaft and a distal end attached to the distal end of the second elongate body.

Example 8 is the medical device of Example 7, wherein the expandable member is a balloon.

Example 9 is the medical device of any of Examples 7 and 8, wherein the first elongate body is configured to supply fluid and is in fluid communication with the expandable member.

In an Example 10, a medical device, including a handle, a housing disposed in the handle, a catheter shaft coupled to the housing, a guidewire situated at least partially in the catheter shaft and having a guidewire distal end that protrudes from the catheter shaft, an element movably coupled to the handle and secured to the guidewire to move the guidewire longitudinally in the catheter shaft, an injection coil situated at least partially in the catheter shaft and having a coil distal end engaged with the guidewire adjacent the guidewire distal end, and a service loop ring. Where the injection coil is looped through the service loop ring to form a service loop that expands and contracts as the guidewire and the injection coil are moved longitudinally in the catheter shaft.

Example 11 is the medical device of Example 10, wherein the service loop ring includes one or more of plastic tubing, a thermoplastic, a thermoset plastic, and metal.

Example 12 is the medical device of any of Examples 10 and 11, wherein the housing has a first opening that receives the guidewire that extends through the housing and into the catheter shaft and the housing has a second opening that receives the injection coil that extends through the housing and into the catheter shaft.

In an Example 13, a method of manufacturing a medical device, including inserting a first elongate body through at least part of a catheter shaft, inserting a proximal end of the first elongate body through a service loop ring a first time, forming a loop with the first elongate body, and inserting the proximal end of the first elongate body through the service loop ring a second time to form a service loop configured to expand and contract as the first elongate body moves longitudinally in the catheter shaft.

Example 14 is the method of Example 13, including inserting a second elongate body through at least part of the catheter shaft, and engaging a distal end of the first elongate body to the second elongate body adjacent a distal end of the second elongate body.

Example 15 is the method of Example 14, including attaching a proximal end of an expandable member to a distal end of the catheter shaft, and attaching a distal end of the expandable member to the distal end of the second elongate body, wherein the first elongate body is configured to supply fluid and in fluid communication with the expandable member.

In an Example 16, a medical device, including a catheter body having a catheter shaft, a first elongate body that extends through at least part of the catheter shaft and is configured to move longitudinally in the catheter shaft, and a service loop ring. Where the first elongate body is looped through the service loop ring to form a service loop configured to expand and contract as the first elongate body moves longitudinally in the catheter shaft.

Example 17 is the medical device of Example 16, wherein the service loop ring is a tubular piece of material.

Example 18 is the medical device of Example 16, including a housing coupled to the catheter shaft and wherein the service loop ring and the service loop are disposed in the housing.

Example 19 is the medical device of Example 16, wherein the first elongate body is a fluid injection coil.

Example 20 is the medical device of Example 16, including a second elongate body that extends through at least part of the catheter shaft and has a distal end that protrudes from the catheter shaft, wherein the second elongate body is configured to move longitudinally in the catheter shaft and a distal end of the first elongate body is engaged adjacent the distal end of the second elongate body.

Example 21 is the medical device of Example 20, including a handle and an element movably coupled to the handle, wherein the element is coupled to the second elongate body to move the second elongate body longitudinally in the catheter shaft.

Example 22 is the medical device of Example 20, including a housing coupled to the catheter shaft and wherein the housing receives the first elongate body that extends through the housing and into the catheter shaft and the housing receives the second elongate body that extends through the housing and into the catheter shaft.

Example 23 is the medical device of Example 20, including an expandable member having a proximal end attached to a distal end of the catheter shaft and a distal end attached to the distal end of the second elongate body.

Example 24 is the medical device of Example 23, wherein the expandable member is a balloon.

Example 25 is the medical device of Example 23, wherein the first elongate body is configured to supply fluid and is in fluid communication with the expandable member.

In an Example 26, a medical device, including a handle, a housing disposed in the handle, a catheter shaft coupled to the housing, a guidewire situated at least partially in the catheter shaft and having a guidewire distal end that protrudes from the catheter shaft, an element movably coupled to the handle and secured to the guidewire to move the guidewire longitudinally in the catheter shaft, an injection coil situated at least partially in the catheter shaft and having a coil distal end engaged with the guidewire adjacent the guidewire distal end, and a service loop ring, wherein the injection coil is looped through the service loop ring to form a service loop that expands and contracts as the guidewire and the injection coil are moved longitudinally in the catheter shaft.

Example 27 is the medical device of Example 26, wherein the service loop ring includes one or more of plastic tubing, a thermoplastic, a thermoset plastic, and metal.

Example 28 is the medical device of Example 26, wherein the service loop ring and the service loop are disposed in the housing.

Example 29 is the medical device of Example 26, wherein the housing has a first opening that receives the guidewire that extends through the housing and into the catheter shaft and the housing has a second opening that receives the injection coil that extends through the housing and into the catheter shaft.

Example 30 is the medical device of Example 26, comprising an expandable member having a proximal end attached to a distal end of the catheter shaft and a distal end attached to the guidewire distal end, such that the injection coil is in fluid communication with the expandable member.

In an Example 31, a method of manufacturing a medical device, including inserting a first elongate body through at least part of a catheter shaft, inserting a proximal end of the first elongate body through a service loop ring a first time, forming a loop with the first elongate body, and inserting the proximal end of the first elongate body through the service loop ring a second time to form a service loop configured to expand and contract as the first elongate body moves longitudinally in the catheter shaft.

Example 32 is the method of Example 31, including inserting a second elongate body through at least part of the catheter shaft, and engaging a distal end of the first elongate body to the second elongate body adjacent a distal end of the second elongate body.

Example 33 is the method of Example 32, including attaching a proximal end of an expandable member to a distal end of the catheter shaft, and attaching a distal end of the expandable member to the distal end of the second elongate body. Where the first elongate body is configured to supply fluid and in fluid communication with the expandable member.

Example 34 is the method of Example 32, including coupling the catheter shaft to a housing, inserting the first elongate body through the housing and into the catheter shaft, and inserting the second elongate body through the housing and into the catheter shaft.

Example 35 is the method of Example 32, including, disposing a housing in a handle, disposing the service loop and the service loop ring in the housing, movably coupling an element to the handle, and coupling the element to the second elongate body to move the first elongate body and the second elongate body longitudinally in the catheter shaft.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
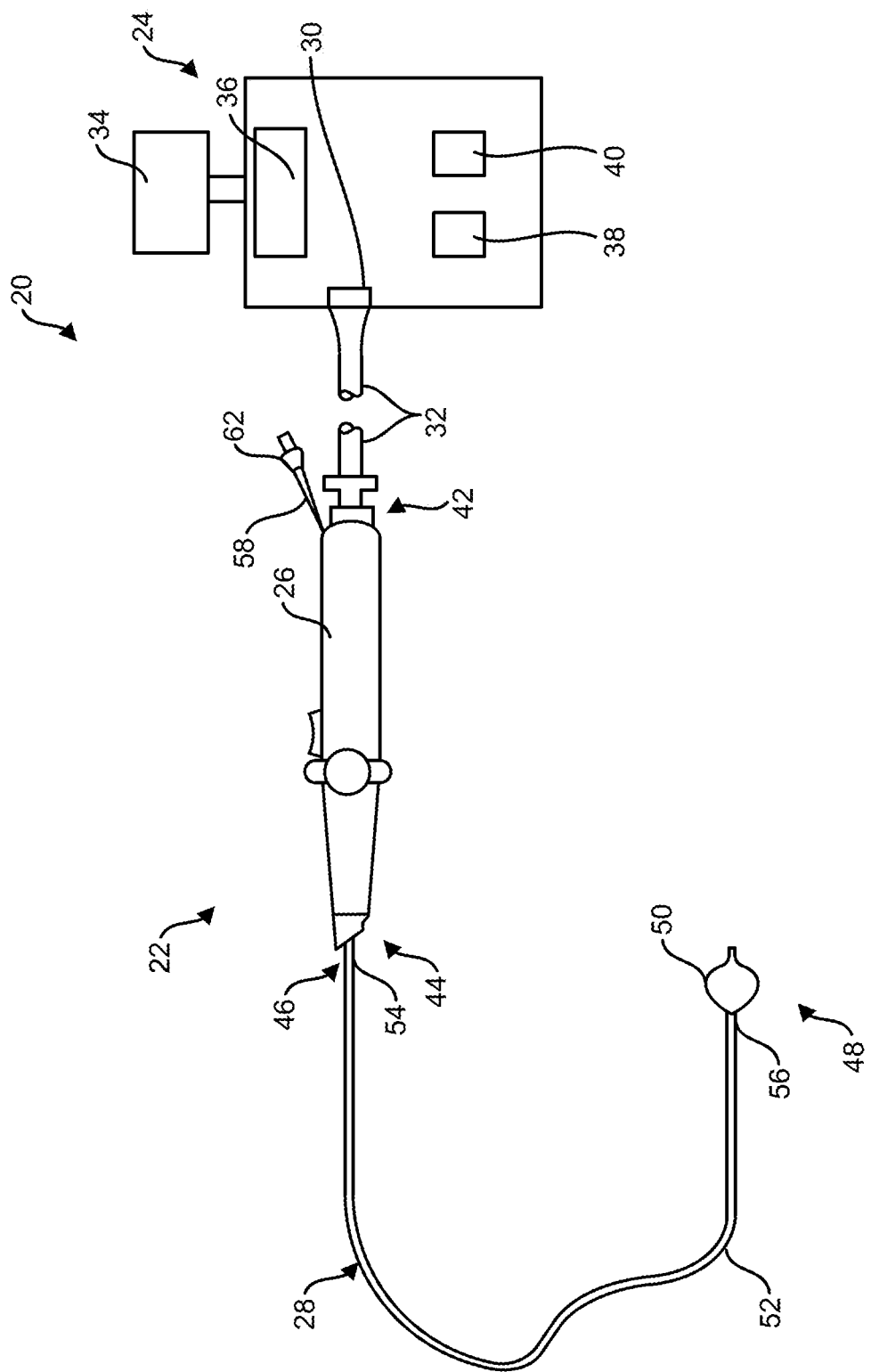
FIG. 1 is a diagram illustrating a system for performing minimally invasive surgical procedures, such as ablation and dilation procedures, according to embodiments of the disclosure.

While the disclosure is amenable to various modifications and alternative forms, specific embodiments have been shown by way of example in the drawings and are described in detail below. The intention, however, is not to limit the disclosure to the embodiments described. On the contrary, the disclosure is intended to cover all modifications, equivalents, and alternatives falling within the scope of the disclosure as defined by the appended claims.

DETAILED DESCRIPTION

FIG. 1 is a diagram illustrating a system 20 for performing minimally invasive surgical procedures, such as ablation and dilation procedures, according to embodiments of the disclosure. The system 20 includes a medical device 22 and a control console 24. The medical device 22 includes a handle 26 and an elongate, flexible catheter 28 configured to be inserted into a patient, such as into the patient's vascular system or into another part of the patient's body. The control console 24 includes a connection 30, such that the medical device 22 can be releasably attached to the control console 24 through the connection 30 and a cable 32.

The medical device 22 includes one or more elongate bodies that extend at least partially through the handle 26 and through at least part of the elongate, flexible catheter 28. These elongate bodies can be one or more of guide wires, conduits, steering wires, and other wires and conduits for performing the functions of the system 20. When the medical device 22 is used, such as during surgery, one or more of these wires and conduits may experience periods of being slack or under tension. The medical device 22 is configured to accommodate and manage the slack and tension by extending and retracting the corresponding wire or conduit.

The control console 24 is configured to provide at least some of the functions of the system 20, such as electrical functions and fluidic functions of the system 20. The control console 24 includes a display 34 and input/output devices 36 that can be used by an operator to control the system 20. In embodiments, the control console 24 includes one or more computers and/or microprocessors 38 and memory 40, such as hard drive and/or solid-state memory. The computers and/or the microprocessors 38 are configured to execute code out of the memory 40 to provide the functions of the system 20.

The handle 26 has a proximal end 42 releasably attached to the connection 30 of the control console 24 by the cable 32 and a distal end 44 attached to the catheter 28. The catheter 28 includes a proximal end 46 attached to the distal end 44 of the handle 26 and a distal end 48 configured to be inserted into the patient, such as into the patient's vascular system or another part of the patient's body. In embodiments, an expandable member 50, such as a balloon, is attached at the distal end 48 of the catheter 28. In embodiments, the expandable member 50 has two layers of material, such that an outer layer of material controls or contains leakage of fluid from the inner layer of material.

The catheter 28 further includes a catheter body 52 having a catheter shaft or lumen therethrough. The catheter body 52 has a proximal end 54 attached or connected to the distal end 44 of the handle 26 and a distal end 56 that is attached to the expandable member 50. In embodiments, the one or more elongate bodies extend through the catheter shaft of the catheter body 52.

Figure 2:
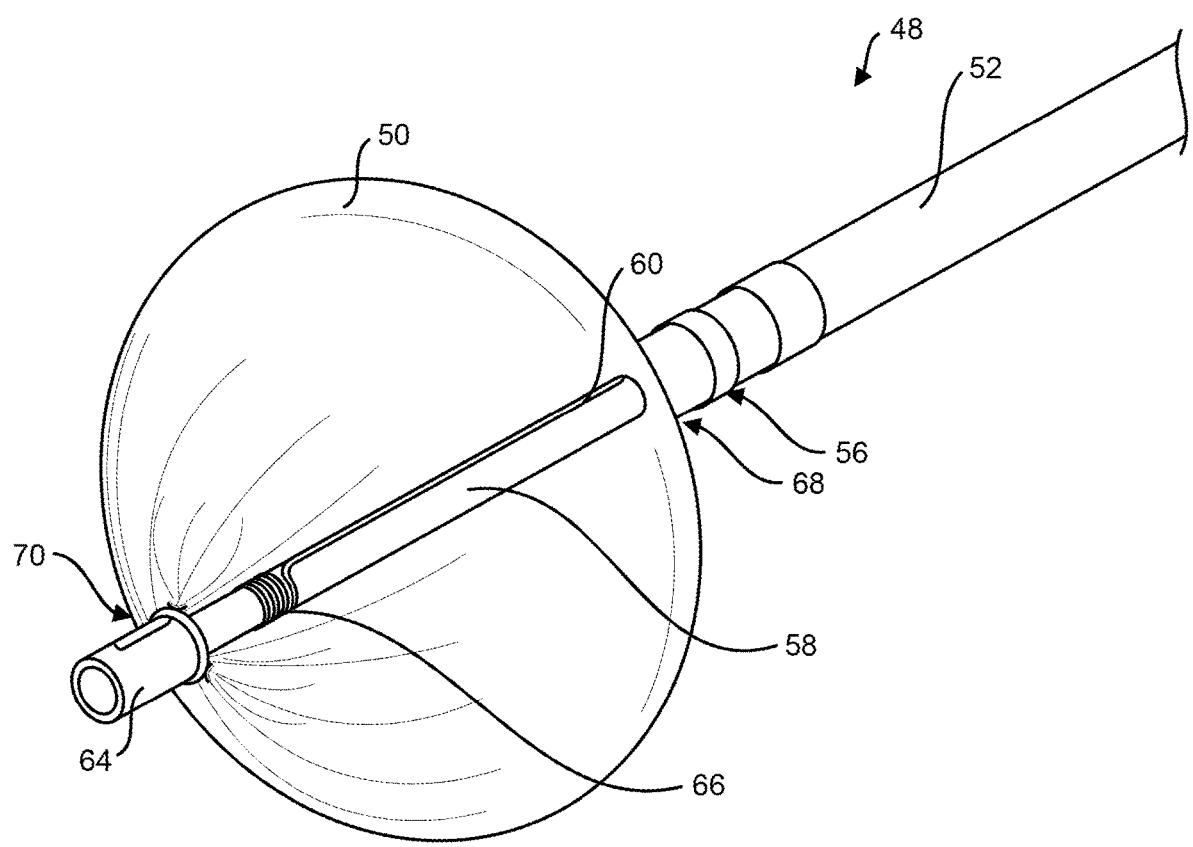
FIG. 2 is a diagram illustrating the distal end of the catheter, according to embodiments of the disclosure.

FIG. 2 is a diagram illustrating the distal end 48 of the catheter 28, according to embodiments of the disclosure. In the example embodiments described herein, the medical device 22 includes a guidewire lumen or guidewire 58 (shown in FIGS. 1 and 2) that is one example of an elongate body and a fluid injection coil or conduit 60 that is another example of an elongate body. In other embodiments, the medical device 22 can include other elongate bodies that utilize the features describe herein.

The guidewire 58 extends into the handle 26 and through the handle 26 into the catheter shaft of the catheter body 52. The guidewire 58 has a proximal end 62 that extends out of the handle 26 (as shown in FIG. 1) and a distal end 64 that protrudes from the distal end 56 of the catheter body 52.

The fluid injection coil 60 is situated in the handle 26 and extends through the handle 26 and into the catheter shaft of the catheter body 52. The fluid injection coil 60 includes a proximal end (not shown in FIGS. 1 and 2) that is fluidically connected to the control console 24 through the connection 30 and the cable 32, and a distal end 66 that is engaged with the guidewire 58 adjacent the guidewire distal end 64. The guidewire 58 and the fluid injection coil 60 are configured to move longitudinally in the catheter shaft of the catheter body 52.

Figure 3:
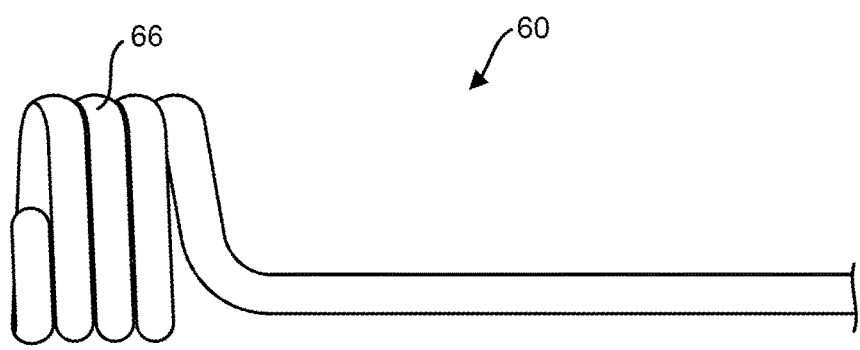
FIG. 3 is a diagram illustrating the distal end of the fluid injection coil, according to embodiments of the disclosure.

FIG. 3 is a diagram illustrating the distal end 66 of the fluid injection coil 60, according to embodiments of the disclosure. The distal end 66 of the fluid injection coil 60 is formed into a coil that is frictionally slid or wound onto the guidewire 58. This frictionally couples the injection coil 60 to the guidewire 58, such that when the guidewire 58 is moved longitudinally in the catheter body 52, the injection coil 60 also moves longitudinally through the catheter body 52 and in relation to the handle 26. In embodiments, the injection coil 60 is not secured to the guidewire 58, such that the guidewire 58 and the injection coil 60 can be moved independently of each other through the catheter body 52.

Referring to FIGS. 1-3, the medical device 22 includes the expandable member 50 having a proximal end 68 that is attached to the distal end 56 of the catheter body 52 and a distal end 70 that is attached to the distal end 64 of the guidewire 58. The distal end 66 of the injection coil 60 is situated inside the expandable member 50 and includes one or more holes for dispensing fluid in the expandable member 50. The injection coil 60 is configured to provide fluid, such as nitrous oxide, from the control console 24 to the interior of the expandable member 50. Thus, the injection coil 60 is in fluid communication with the inside of the expandable member 50, such that the injection coil 60 provides fluid from the control console 24 to expand the expandable member 50. The medical device 22 is further configured to remove the fluid from the expandable member 50 through the catheter shaft of the catheter body 52. In embodiments, the expandable member 50 is a balloon. In embodiments, the expandable member 50 has two layers of material, such that an outer layer of material controls or contains leakage of fluid from the inner layer of material.

In operation, to insert the distal end 48 of the catheter 28 including the expandable member 50 into the patient's body, the expandable member 50 is deflated or in a deflated condition and the distal end 64 of the guidewire 58 is extended out of the distal end 56 of the catheter body 52, which flattens the expandable member 50 prior to insertion in the patient.

Extending the distal end 64 of the guidewire 58 out of the distal end 56 of the catheter body 52, pulls the fluid injection coil 60 out of the distal end 56 of the catheter body 52, such that the injection coil 60 is put under tension and an extra length of the injection coil 60 is pulled out of the handle 26.

With the fluid injection coil 60 fluidically coupled to the control console 24 and in fluid communication with the inside of the expandable member 50, fluid is injected into the expandable member 50 through the injection coil 60 to expand the expandable member 50. This moves the distal end 64 of the guidewire 58 toward the distal end 56 of the catheter body 52. The guidewire 58 slides longitudinally in the catheter body 52 and the handle 26, such that the proximal end 62 of the guidewire 58 moves away from the handle 26. The fluid injection coil 60 is moved back into the catheter body 52 and the handle 26, such that the injection coil 60 experiences slack that is taken up inside the handle 26.

To move the catheter 28 in the patient or remove the catheter 28 from the patient, the expandable member 50 is deflated and the guidewire 58 is extended out of the distal end 56 of the catheter body 52 to flatten the expandable member 50. In this situation, extending the guidewire 58 out of the distal end 56 of the catheter body 52, pulls the fluid injection coil 60 out of the distal end 56 of the catheter body 52, such that the injection coil 60 is put under tension and an extra length of the injection coil 60 is pulled out of the handle 26.

Figure 4:
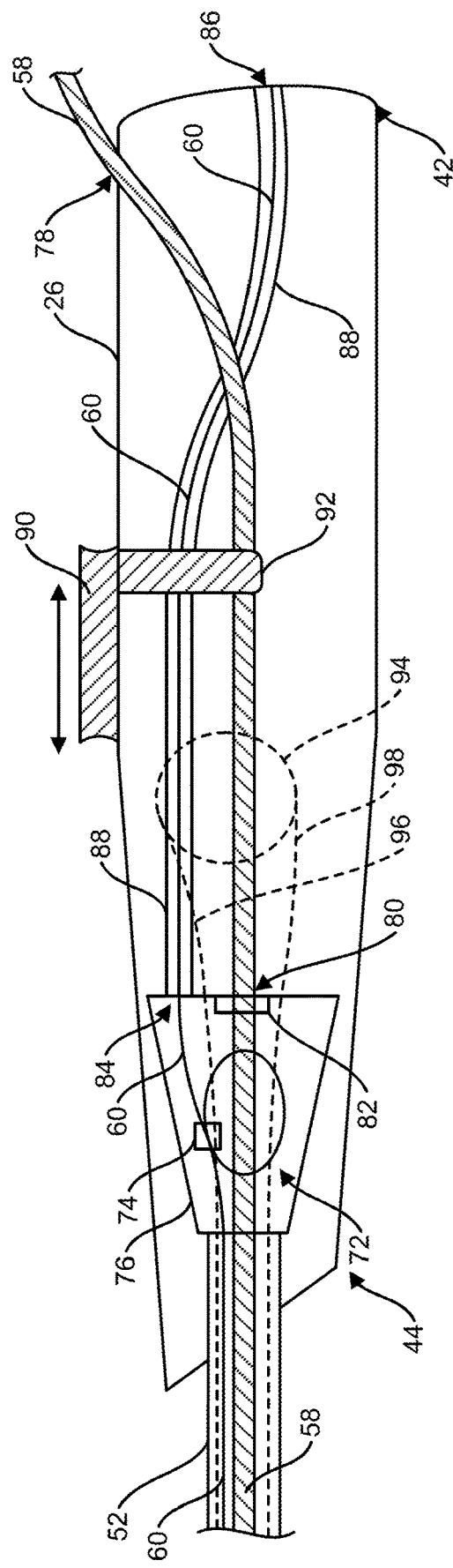
FIG. 4 is a diagram illustrating the handle configured to provide an extra length of injection coil when the injection coil is under tension and to take up slack in the injection coil when the injection coil experiences slack, according to embodiments of the disclosure.
Figure 5:
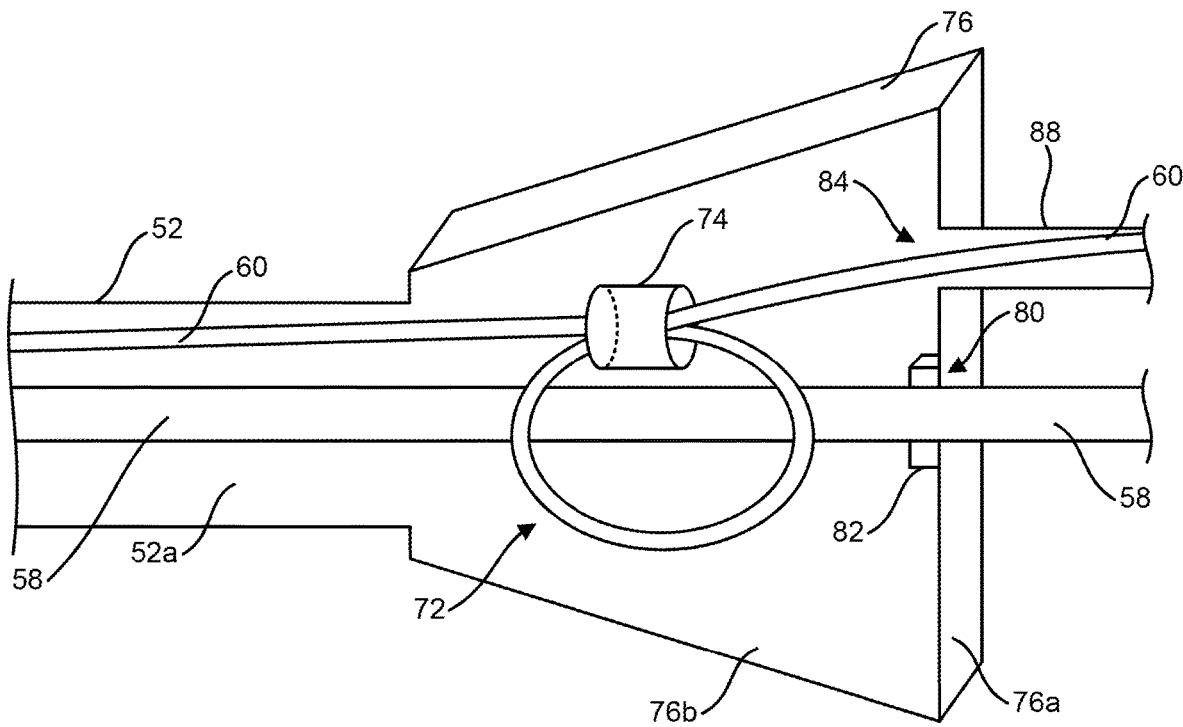
FIG. 5 is a diagram illustrating the housing attached to the catheter body with the guidewire and the injection coil passing through the housing and into the catheter shaft of the catheter body, according to embodiments of the disclosure.

FIG. 4 is a diagram illustrating the handle 26 configured to provide an extra length of injection coil 60 when the injection coil 60 is under tension and to take up slack in the injection coil 60 when the injection coil 60 experiences slack, according to embodiments of the disclosure. The injection coil 60 is formed into a service loop 72 that retracts to a smaller diameter to provide the extra length of the injection coil 60 and expands into a larger diameter to take up the slack in the injection coil 60. The injection coil 60 is looped through a service loop ring 74 to form the service loop 72 of the injection coil 60. The service loop ring 74 maintains and manages the service loop 72 of the injection coil 60 during retraction and expansion of the service loop 72. The service loop ring 74 provides for optimal expansion and retraction of the injection coil 60, such that the service loop 72 can retract to a smaller diameter to provide the extra length of injection coil 60 and expand to a larger diameter to take up slack in the injection coil 60. The medical device 22 includes a chamber or housing 76 that is disposed in the handle 26 and attached to the catheter body 52, as shown in FIGS. 4 and 5. In embodiments, the injection coil 60 is made from or includes a shape memory material, such as nitinol.

FIG. 5 is a diagram illustrating the housing 76 attached to the catheter body 52 with the guidewire 58 and the injection coil 60 passing through the housing 76 and into the catheter shaft of the catheter body 52, according to embodiments of the disclosure. The injection coil service loop 72 and the service loop ring 74 are disposed in the housing 76. In embodiments, the catheter body 52 is sealed to the housing 76, such that the inside of the housing 76 is in fluid communication with the catheter shaft of the catheter body 52.

Referring to FIGS. 4 and 5, the guidewire 58 extends through an opening 78 in the handle 26 near the proximal end 42 of the handle 26 and into an opening 80 in the housing 76. The guidewire 58 further extends through the housing 76 and into the catheter shaft of the catheter body 52. The guidewire 58 is configured to move or slide through the handle 26 and the housing 76 and the catheter body 52. In embodiments, the housing 76 includes a seal 82, such as an O-ring seal, that surrounds the guidewire 58 to prevent fluid from leaking out of the housing 76 at the opening 80 and around the guidewire 58.

The fluid injection coil 60 extends from the proximal end 42 of the handle 26 into an opening 84 in the housing 76. The fluid injection coil 60 is looped through the service loop ring 74 to form the service loop 72, which is situated in the housing 76. The fluid injection coil 60 extends through the housing 76 and into the catheter shaft of the catheter body 52. The proximal end 86 of the fluid injection coil 60 is secured or attached to the proximal end 42 of the handle 26, such that the fluid injection coil 60 can be fluidically connected to the control console 24 through the connection 30 and the cable 32 to provide fluid to the expandable member 50.

A tube 88 surrounds the injection coil 60 from the proximal end 42 of the handle 26 to the housing 76. The tube 88 is sealed to the housing 76 at the opening 84 and sealed to the proximal end 42 of the handle 26, such that the tubing 88 can be fluidically connected to the control console 24 through the connection 30 and the cable 32 to remove fluid from the expandable member 50. In embodiments, the housing 76 is a sealed unit, such that the housing 76 is sealed to the catheter body 52, and sealed around the guidewire 58, and sealed to the tubing 88 for removing fluid from the expandable member 50 through the catheter shaft of the catheter body 52 and the housing 76 and the tubing 88 to the control console 24 through the connection 30 and the cable 32. In other embodiments, the housing 76 includes one or more other tubes that are sealed to the housing 76 to remove fluid from the expandable member 50 and not the tubing 88. Also, in embodiments, the housing 76 includes a seal, such as an O-ring seal, that surrounds the fluid injection coil 60 to prevent fluid from leaking out of the housing 76 at the opening 84 and around the injection coil 60.

As previously described, the distal end 66 of the injection coil 60 is engaged with the guidewire 58 adjacent the guidewire distal end 64 and the guidewire 58 and the fluid injection coil 60 are configured to move together longitudinally in the catheter shaft of the catheter body 52.

The handle 26 further includes an element 90, such as a knob, that is movably coupled to the handle 26 and secured at 92 to the guidewire 58. The element 90 is slid back and forth, as indicated by the arrow, to move the guidewire 58 through the handle 26 and the housing 76 and the catheter body 52. Where, the guidewire 58 is free to slide in and out of the handle 26 at opening 78 near the proximal end 42 of the handle 26.

If the element 90 is moved toward the distal end 44 of the handle 26, the guidewire 58 and the injection coil 60 are moved in the catheter body 52, such that the distal end 64 of the guidewire 58 is moved further away from the distal end 56 of the catheter body 52, and the distal end 66 of the injection coil 60 is moved further away from the distal end 56 of the catheter body 52. Since, the proximal end 86 of the fluid injection coil 60 is fixed to the proximal end 42 of the handle 26, the injection coil 60 is not free to slide in and out of the handle 26 at the proximal end 42 of the handle 26 and moving the distal end 66 of the injection coil 60 further away from the distal end 56 of the catheter body 52 pulls an extra length of the injection coil 60 out of the handle 26, retracting the diameter of the service loop 72. The service loop ring 74 maintains and manages the shape of the service loop 72 as the injection coil 60 is pulled out of the handle 26 and the diameter of the service loop 72 decreases.

If the element 90 is moved toward the proximal end 42 of the handle 26, such as when the expandable member 50 is inflated, the guidewire 58 and the injection coil 60 are moved in the catheter body 52, such that the distal end 64 of the guidewire 58 is moved closer to the distal end 56 of the catheter body 52, and the distal end 66 of the injection coil 60 is moved closer to the distal end 56 of the catheter body 52. Since, the proximal end 86 of the fluid injection coil 60 is fixed to the proximal end 42 of the handle 26, the injection coil 60 is not free to slide in and out of the handle 26 at the proximal end 42 of the handle 26, and moving the distal end 66 of the injection coil 60 closer to the distal end 56 of the catheter body 52 puts slack into the injection coil 60. The diameter of the service loop 72 expands to take up the slack in the injection coil 60 and put more of the injection coil 60 in the housing 76. The service loop ring 74 maintains and manages the shape of the service loop 72 as the injection coil 60 is put back into the handle 26 and the diameter of the service loop 72 increases.

In embodiments, the handle 26 includes other knobs and elements for controlling other functions of the medical device 22. For example, the handle 26 can include a control knob 94 for moving steering wires 96 and 98 in the catheter body 52 to manipulate the catheter body 52 through the patient's vascular system or through other parts of the patient's body. In embodiments, the housing 76 includes a seal, such as an O-ring seal, around each of the steering wires 96 and 98 to prevent fluid leakage around the steering wires 96 and 98. In embodiments, the housing 76 includes a fitting or is otherwise configured around each of the steering wires 96 and 98 to prevent fluid leakage around the steering wires 96 and 98.

The housing 76 includes a housing endplate 76a that is sealed onto the housing body 76b. The housing endplate 76a includes the openings for the guidewire 58, the fluid injection coil 60, and other wires and conduits, such as the steering wires 96 and 98. The housing endplate 76a includes seals or is configured to seal around each of the wires and conduits to prevent fluid from leaking out around the wires and conduits. Also, in embodiments, the tubing 88 is sealed to the housing endplate 76a to prevent leakage of fluids around the tubing 88 and the fluid injection coil 60. Thus, in embodiments, fluid, such as nitrous oxide, from the expandable member 50 is or can be removed through the catheter shaft 52a of the catheter body 52 to the sealed housing 76 and through the tubing 88 to the control console 24. In embodiments that do not include the tubing 88, another tube or passage way can be sealed to the housing endplate 76a to remove the fluid from the housing 76 and to the control console 24.

Figure 6:
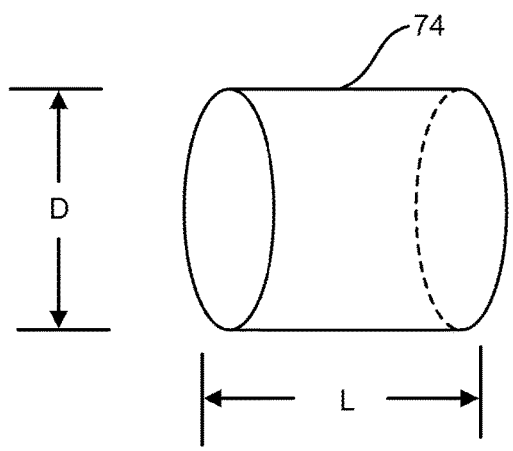
FIG. 6 is a diagram illustrating the service loop ring, according to embodiments of the disclosure.

FIG. 6 is a diagram illustrating the service loop ring 74, according to embodiments of the disclosure. The service loop ring 74 is a hollow piece of material configured to have an elongate body, such as the fluid injection coil 60, looped through the service loop ring 74 to form a service loop 72. In embodiments, the service loop ring 74 is a tubular piece of material. In embodiments, the service loop ring 74 is made from a flexible polymer tubing, such as Tygon™. In embodiments, the service loop ring 74 is made from or includes one of the following or a combination of the following: 1) elastomers that are block copolymers made up of rigid polyamide blocks and soft polyether blocks, which can be manipulated (including their relative ratio) for the creation of a large range that spans the flexibility spectrum from very hard and rigid to very soft and flexible, without the need for plasticizers, such as PEBAX™, and 2) thermoplastic polyurethane elastomers, such as PELLETHANE™. In embodiments, the service loop ring 74 is made from or includes one or more of a thermoplastic, a thermoset plastic, and metal. In embodiments, the service loop ring 74 is made from or includes one or more of polycarbonate, nylon, and acrylic. In other embodiments, the service loop ring 74 can be made from another material, such as another plastic.

The service loop ring 74 is sized to maintain the shape of the service loop 72 of the elongate body, such as the fluid injection coil 60, when the service loop 72 is retracted to have a smaller diameter and when the service loop 72 is expanded to have a larger diameter. In embodiments, the service loop ring 74 has a length L in a range from 0.05 inches to 0.075 inches. In embodiments, the service loop ring 74 has a diameter D of 1/16 inches.

Figure 7:
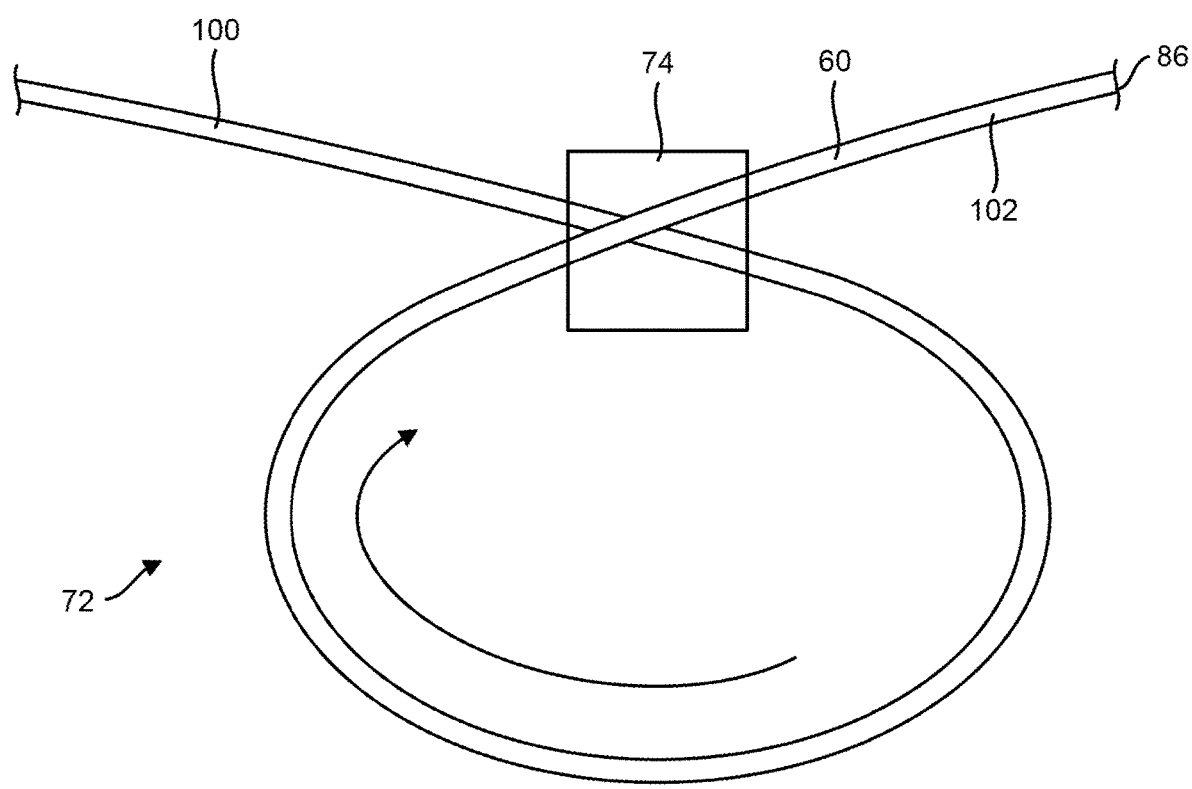
FIG. 7 is a diagram illustrating the fluid injection coil inserted through the service loop ring to form a service loop, according to embodiments of the disclosure.

FIG. 7 is a diagram illustrating the fluid injection coil 60 inserted through the service loop ring 74 to form a service loop 72, according to embodiments of the disclosure. In embodiments, to form the service loop 72 in the fluid injection coil 60, the service loop ring 74 is first inserted over the proximal end 86 of the fluid injection coil 60 and slid further onto the fluid injection coil 60. Next, the proximal end 86 of the fluid injection coil 60 is pulled around in a circle to form a loop in the injection coil 60 and the proximal end 86 of the injection coil 60 is inserted a second time through the service loop ring 74. This forms the service loop 72 in the fluid injection coil 60. In embodiments, the proximal end 86 of the fluid injection coil 60 is pulled until the service loop 72 is roughly 0.5 inches in diameter.

The service loop 72 can then be inserted into the housing 76 with the distal end 66 of the fluid injection coil 60 inserted through the catheter body 52 and the service loop 72 situated in the housing 76. A proximal face of the housing 76 can be put on the housing 76, with the fluid injection coil 60 inserted through the opening 84 and the tubing 88 inserted over the fluid injection coil 60 between the housing 76 and the proximal end 42 of the handle 26. In embodiments, the distal portion of the fluid injection coil 60, indicated at 100, is positioned below the loop and the proximal portion of the fluid injection coil 60, indicated at 102.

Figure 8:
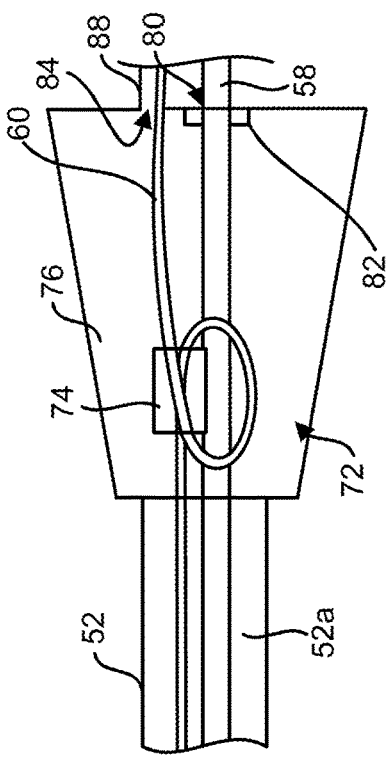
FIG. 8 is a diagram illustrating the guidewire and the fluid injection coil, including the service loop, prior to insertion of the catheter into the patient's body or prior to movement of the catheter in the patient's body, according to embodiments of the disclosure.
Figure 8:
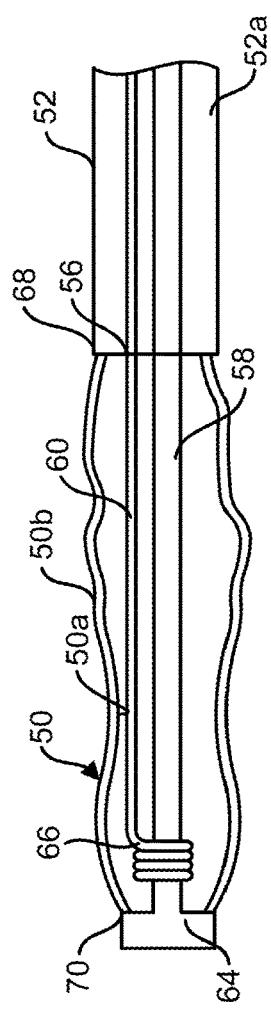
Figure 9:
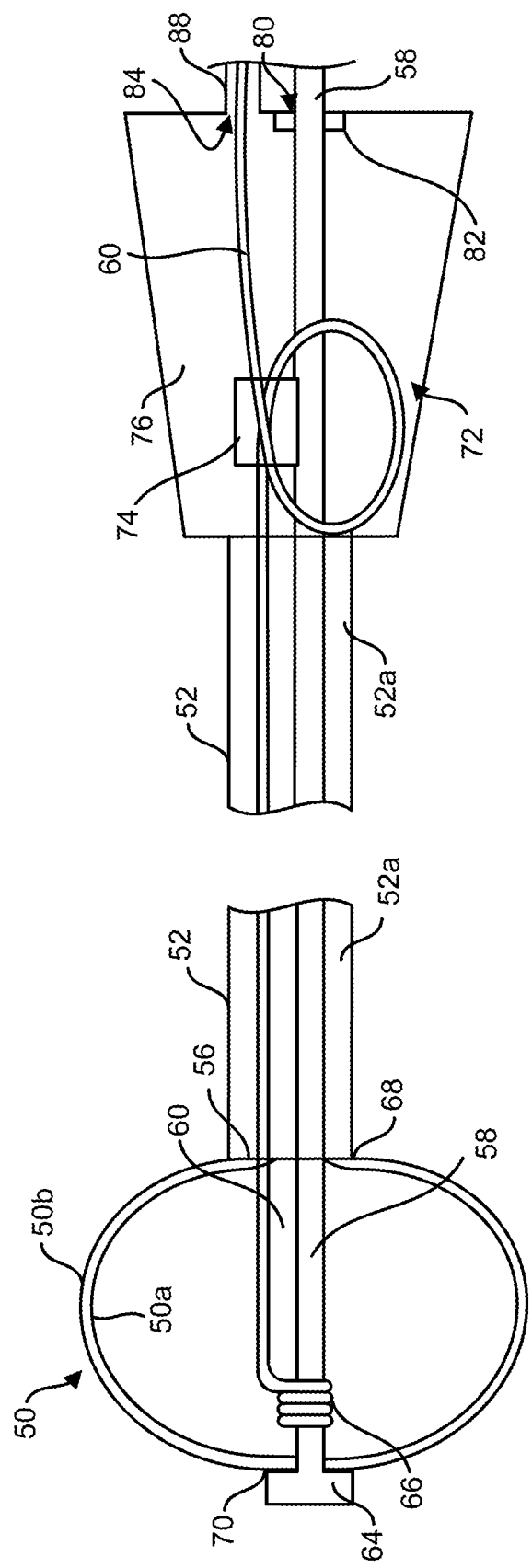
FIG. 9 is a diagram illustrating the guidewire and the fluid injection coil, including the service loop, and the expandable member after the expandable member has been inflated, according to embodiments of the disclosure.

FIGS. 8 and 9 are diagrams illustrating the operation of the service loop 72 of the fluid injection coil 60, according to embodiments of the disclosure. As illustrated in FIGS. 8 and 9, the guidewire 58 extends through the opening 80 in the housing 76 and into the catheter shaft of the catheter body 52. The distal end 64 of the guidewire 58 protrudes from the distal end 56 of the catheter body 52 and is attached to the distal end 70 of the expandable member 50. The proximal end 68 of the expandable member 50 is attached to the distal end 56 of the catheter body 52. In embodiments, the housing 76 also includes the seal 82 that surrounds the guidewire 58 to prevent fluid from leaking out of the housing 76 at the opening 80 and around the guidewire 58. In some embodiments, the expandable member 50 is a balloon and, in some embodiments, the expandable member 50 has two layers of material 50a and 50b, such that the outer layer of material 50b controls or contains leakage of fluid from the inner layer of material 50a.

The fluid injection coil 60 extends into the opening 84 in the housing 76 and is looped through the service loop ring 74 to provide the service loop 72, which is situated in the housing 76. The fluid injection coil 60 extends through the housing 76 and into the catheter shaft of the catheter body 52. The proximal end 86 of the fluid injection coil 60 is secured or attached to the proximal end 42 of the handle 26, such that the fluid injection coil 60 can be fluidically connected to the control console 24 through the connection 30 and the cable 32 to provide fluid to the expandable member 50. In embodiments, the tube 88 surrounds the injection coil 60 from the proximal end 42 of the handle 26 to the housing 76. The distal end 66 of the fluid injection coil 60 is engaged with the guidewire 58 adjacent the guidewire distal end 64, such that the guidewire 58 and the fluid injection coil 60 can move together, longitudinally, in the catheter shaft of the catheter body 52.

FIG. 8 is a diagram illustrating the guidewire 58 and the fluid injection coil 60, including the service loop 72, prior to insertion of the catheter 28 into the patient's body or prior to movement of the catheter 28 in the patient's body, according to embodiments of the disclosure.

In operation, the expandable member 50 is either in a deflated condition or deflated through the catheter shaft 52a of the catheter body 52 and the housing 76 and the tubing 88 to the control console 24. In embodiments, the control console 24 includes a vacuum or a vacuum pump coupled to the tubing 88 for deflating the expandable member 50.

By moving the element 90 toward the distal end 44 of the handle 26, the guidewire 58 and the injection coil 60 are moved in the catheter body 52, such that the distal end 64 of the guidewire 58 is moved further away from the distal end 56 of the catheter body 52, and the distal end 66 of the injection coil 60 is moved further away from the distal end 56 of the catheter body 52. Moving the distal end 64 of the guidewire 58 away from the distal end 56 of the catheter body 52 further flattens the expandable member 50.

Since, the proximal end 86 of the fluid injection coil 60 is fixed to the proximal end 42 of the handle 26, the injection coil 60 is not free to slide in and out of the handle 26, such that moving the distal end 66 of the injection coil 60 further away from the distal end 56 of the catheter body 52 puts tension on the fluid injection coil 60 and pulls an extra length of the injection coil 60 out of the housing 76. This extra length of the injection coil 60 is provided by the service loop 72, where the diameter of the service loop 72 decreases or gets smaller to provide the extra length of the fluid injection coil 60. The service loop ring 74 maintains and manages the shape of the service loop 72 as the injection coil 60 is pulled out of the handle 26 and the diameter of the service loop 72 decreases. Next, the catheter 28 can be steered to a site of interest in the patient's body and the expandable member 50 can be inflated.

FIG. 9 is a diagram illustrating the guidewire 58 and the fluid injection coil 60, including the service loop 72, and the expandable member 50 after the expandable member 50 has been inflated, according to embodiments of the disclosure.

With the fluid injection coil 60 fluidically coupled to the control console 24 and in fluid communication with the inside of the expandable member 50, fluid is injected into the expandable member 50 through the injection coil 60 to expand the expandable member 50. This expansion of the expandable member 50 moves the guidewire 58 and the injection coil 60 in the catheter body 52, such that the distal end 64 of the guidewire 58 is moved closer to the distal end 56 of the catheter body 52, and the distal end 66 of the injection coil 60 is moved closer to the distal end 56 of the catheter body 52. Also, the element 90 is moved toward the proximal end 42 of the handle 26. In embodiments, the operator can assist expansion of the expandable member 50 by moving the element 90 toward the proximal end 42 of the handle 26.

Since, the proximal end 86 of the fluid injection coil 60 is fixed to the proximal end 42 of the handle 26, the injection coil 60 is not free to slide in and out of the handle 26 at the proximal end 42 of the handle 26, and moving the distal end 66 of the injection coil 60 closer to the distal end 56 of the catheter body 52 puts slack into the injection coil 60. The diameter of the service loop 72 expands to take up the slack in the injection coil 60 and put more of the injection coil 60 in the housing 76. The service loop ring 74 maintains and manages the shape of the service loop 72 as the injection coil 60 is put back into the handle 26 and the diameter of the service loop 72 increases.

Figure 10:
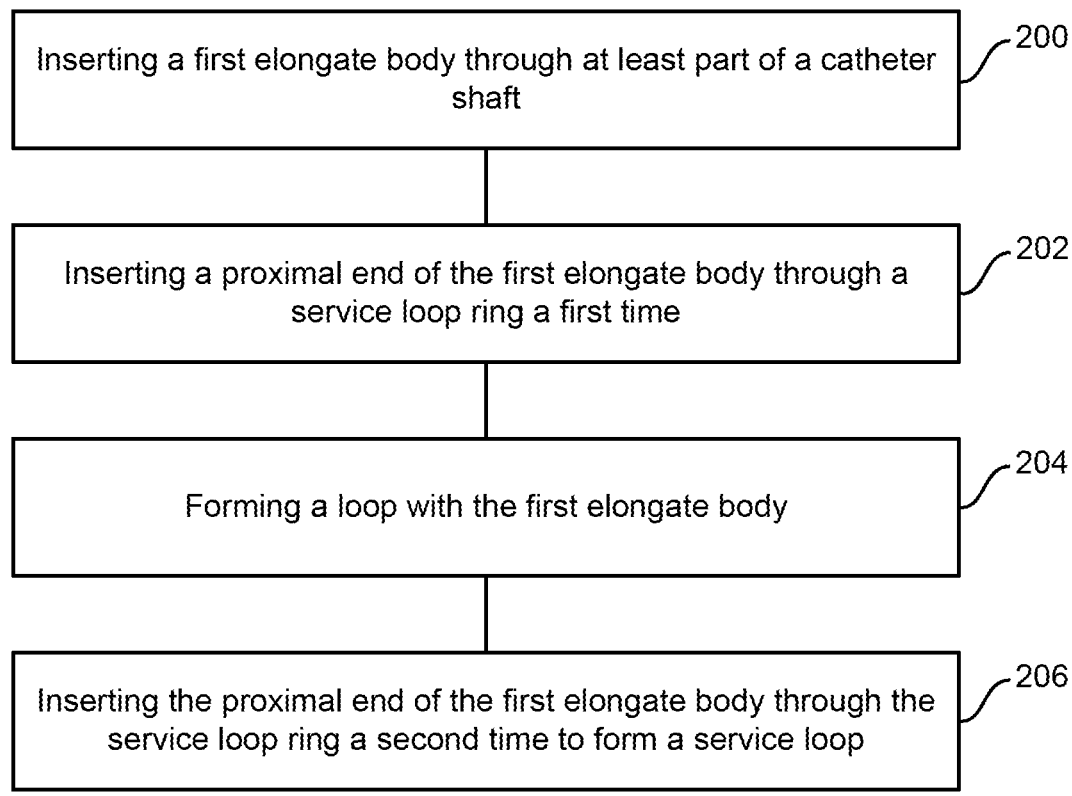
FIG. 10 is a flowchart diagram illustrating a method of manufacturing a medical device, according to embodiments of the disclosure.

FIG. 10 is a flowchart diagram illustrating a method of manufacturing a medical device, such as medical device 22, according to embodiments of the disclosure. In embodiments, the medical device includes one or more of a first elongate body, a second elongate body, a catheter shaft, and an expandable member. In embodiments, the first elongate body is the fluid injection coil 60. In embodiments, the second elongate body is the guidewire 58. In embodiments, the catheter shaft is the catheter shaft 52a of the catheter body 52. In embodiments, the expandable member is the expandable member 50. In other embodiments, one or more of the first elongate body and the second elongate body can be other suitable wires or conduits.

At 200, the method includes inserting a first elongate body through at least part of a catheter shaft. In embodiments, this includes inserting the fluid injection coil 60 through at least part of the catheter shaft 52a of the catheter body 52.

Also, in embodiments, the method includes inserting a second elongate body through at least part of the catheter shaft and engaging a distal end of the first elongate body to the second elongate body adjacent a distal end of the second elongate body. In embodiments, this includes inserting the guidewire 58 through at least part of the catheter shaft 52a and engaging the distal end 66 of the injection coil 60 to the guidewire 58 adjacent the distal end 64 of the guidewire 58.

Also, in embodiments, the method includes attaching a proximal end of an expandable member to a distal end of the catheter shaft and attaching a distal end of the expandable member to the distal end of the second elongate body, where the first elongate body is configured to supply fluid and is in fluid communication with the expandable member. In embodiments, this includes attaching the proximal end 68 of the expandable member 50 to the distal end 56 of the catheter shaft 52a and attaching the distal end 70 of the expandable member 50 to the distal end 64 of the guidewire 58, where the fluid injection coil 60 is configured to supply fluid and is in fluid communication with the expandable member 50.

At 202, the method includes inserting a proximal end of the first elongate body through a service loop ring a first time. Where, in embodiments, this includes inserting the proximal end 86 of the fluid injection coil 60 through the service loop ring 74 or putting the service loop ring 74 over the proximal end 86 of the fluid injection coil 60 and sliding the service loop ring 74 further onto the injection coil 60.

At 204, the method includes forming a loop with the first elongate body and, at 206, the method includes inserting the proximal end of the first elongate body through the service loop ring a second time to form a service loop that is configured to expand and contract as the first elongate body moves longitudinally in the catheter shaft. In embodiments, at 204, this includes forming a loop with the injection coil 60 and, at 206, this includes inserting the proximal end 86 of the fluid injection coil 60 through the service loop ring 74 a second time to form the service loop 72 of the injection coil 60, which is configured to expand and contract as the injection coil 60 moves longitudinally in the catheter shaft 52a of the catheter body 52.

In embodiments, the method further includes coupling the catheter shaft to a housing, inserting the first elongate body through the housing and into the catheter shaft, and inserting the second elongate body through the housing and into the catheter shaft. In embodiments, this includes coupling the catheter shaft 52a to a housing 76, inserting the fluid injection coil 60 through the housing 76 and into the catheter shaft 52a, and inserting the guidewire 58 through the housing 76 and into the catheter shaft 52a.

Also, in embodiments, the method includes disposing a housing in a handle, disposing the service loop and the service loop ring in the housing, movably coupling an element to the handle, and coupling the element to the second elongate body to move the first elongate body and the second elongate body longitudinally in the catheter shaft. In embodiments, this includes disposing a housing 76 in a handle 26, disposing the service loop 72 and the service loop ring 74 in the housing 76, movably coupling an element 90 to the handle 26, and coupling the element 90 to the guidewire 58 to move the fluid injection coil 60 and the guidewire longitudinally in the catheter shaft 52a.

Various modifications and additions can be made to the exemplary embodiments discussed without departing from the scope of the present disclosure. For example, while the embodiments described above refer to certain features, the scope of this disclosure also includes embodiments having different combinations of features and embodiments that do not include all the described features. Accordingly, the scope of the present disclosure is intended to embrace all such alternatives, modifications, and variations as fall within the scope of the claims, together with all equivalents thereof.

What is claimed is:

1. A medical device, comprising:
a handle defining a housing;
a catheter body having a catheter shaft extending distally from the handle;
a first elongate body that extends through at least part of the catheter shaft and is configured to move longitudinally in the catheter shaft and includes a service loop formed in a portion thereof, the service loop disposed within the housing and configured to expand and contract as the first elongate body moves longitudinally in the catheter shaft; and
a tubular service loop ring disposed within the housing, the service loop ring having a first end, a second end opposite the first end, and a lumen extending from the first end to the second end, wherein the first elongate body includes a first portion passing through the first and second ends and the lumen of the service loop ring, and a second portion passing through the first and second ends and the lumen of the service loop ring, and crossing over the first portion of the first elongate body within the lumen of the service loop ring, and wherein the service loop is formed between the first portion and the second portion of the first elongate body and is located externally of the service loop ring.

2. The medical device of claim 1, wherein the first elongate body is a fluid injection coil.

3. The medical device of claim 1, comprising a second elongate body that extends through at least part of the catheter shaft and has a distal end that protrudes from the catheter shaft, wherein the second elongate body is configured to move longitudinally in the catheter shaft and a distal end of the first elongate body is engaged adjacent the distal end of the second elongate body.

4. The medical device of claim 3, comprising an element movably coupled to the handle, wherein the element is coupled to the second elongate body to move the second elongate body longitudinally in the catheter shaft.

5. The medical device of claim 3, wherein the housing receives the first elongate body that extends through the housing and into the catheter shaft and the housing receives the second elongate body that extends through the housing and into the catheter shaft.

6. The medical device of claim 3, comprising an expandable member having a proximal end attached to a distal end of the catheter shaft and a distal end attached to the distal end of the second elongate body.

7. The medical device of claim 6, wherein the expandable member is a balloon.

8. The medical device of claim 6, wherein the first elongate body is configured to supply fluid and is in fluid communication with the expandable member.

9. A medical device, comprising:
a handle;
a housing disposed in the handle;
a catheter shaft coupled to the housing;
a guidewire situated at least partially in the catheter shaft and having a guidewire distal end that protrudes from the catheter shaft;
an element movably coupled to the handle and secured to the guidewire to move the guidewire longitudinally in the catheter shaft;
an injection coil situated at least partially in the catheter shaft and having a coil distal end engaged with the guidewire adjacent the guidewire distal end; and
a tubular service loop ring disposed within the housing, the service loop ring having a first end, and opposite second end, and a lumen extending through the service loop ring from the first end to the second end, wherein the injection coil includes a first portion passing through the first and second ends and the lumen of the service loop ring, a second portion passing through the first and second ends and the lumen of the service loop ring and crossing over the first portion of the injection coil within the lumen of the service loop ring, and a service loop formed between the first portion of the injection coil and the second portion of the injection coil and located externally of the service loop ring, wherein the service loop is configured to expand and contract as the guidewire and the injection coil are moved longitudinally in the catheter shaft.

10. The medical device of claim 9, wherein the service loop ring includes one or more of plastic tubing, a thermoplastic, a thermoset plastic, and metal.

11. The medical device of claim 9, wherein the service loop ring and the service loop are disposed in the housing.

12. The medical device of claim 9, wherein the housing has a first opening that receives the guidewire that extends through the housing and into the catheter shaft and the housing has a second opening that receives the injection coil that extends through the housing and into the catheter shaft.

13. The medical device of claim 9, comprising an expandable member having a proximal end attached to a distal end of the catheter shaft and a distal end attached to the guidewire distal end, such that the injection coil is in fluid communication with the expandable member.

* * * * *